(12) United States Patent
Gross

(10) Patent No.: US 8,145,321 B2
(45) Date of Patent: Mar. 27, 2012

(54) IMPLANT AND DELIVERY TOOL THEREFOR

(75) Inventor: Yossi Gross, Moshav Mazor (IL)

(73) Assignee: Yossi Gross, Moshav Mazor (IL)

(*) Notice: Subject to any disclaimer, the term of this patent is extended or adjusted under 35 U.S.C. 154(b) by 348 days.

(21) Appl. No.: 12/588,518

(22) Filed: Oct. 19, 2009

(65) Prior Publication Data

US 2010/0100195 A1    Apr. 22, 2010

Related U.S. Application Data

(63) Continuation of application No. 11/325,731, filed on Jan. 5, 2006, now Pat. No. 7,632,297, which is a continuation of application No. 10/736,740, filed on Dec. 17, 2003, now Pat. No. 7,004,965.

(51) Int. Cl.
  *A61F 2/00* (2006.01)
  *A61F 2/06* (2006.01)
(52) U.S. Cl. .................. 607/101; 623/1.11
(58) Field of Classification Search .......... 607/96, 607/98, 99, 101, 102, 156; 623/1.11, 1.15, 623/1.42
See application file for complete search history.

(56) References Cited

U.S. PATENT DOCUMENTS

| | | | |
|---|---|---|---|
| 4,978,323 A | 12/1990 | Freedman | |
| 5,160,341 A | 11/1992 | Brenneman et al. | |
| 5,601,591 A | 2/1997 | Edwards et al. | |
| 5,776,142 A | 7/1998 | Gunderson | |
| 6,119,045 A | 9/2000 | Bolmsjo | |
| 6,231,516 B1 | 5/2001 | Keilman et al. | |
| 6,258,094 B1 | 7/2001 | Nicholson et al. | |
| 6,280,465 B1 | 8/2001 | Cryer | |
| 6,517,566 B1 | 2/2003 | Hovland et al. | |
| 6,679,851 B2 | 1/2004 | Brubank et al. | |
| 6,702,846 B2 | 3/2004 | Mikus et al. | |
| 6,709,452 B1 | 3/2004 | Valimaa et al. | |
| 6,991,647 B2 | 1/2006 | Jadhav | |
| 7,004,965 B2 | 2/2006 | Gross | |
| 7,104,949 B2 | 9/2006 | Anderson et al. | |
| 7,175,589 B2 | 2/2007 | Deem et al. | |
| 7,585,271 B2 * | 9/2009 | Gerber et al. | 600/30 |
| 7,632,297 B2 | 12/2009 | Gross | |
| 2002/0177904 A1 | 11/2002 | Huxel et al. | |
| 2003/0144658 A1 | 7/2003 | Schwartz et al. | |
| 2004/0133263 A1 | 7/2004 | Dusbabek et al. | |
| 2004/0181287 A1 | 9/2004 | Gellman | |
| 2004/0254520 A1 | 12/2004 | Porteous et al. | |
| 2005/0216074 A1 | 9/2005 | Sahatjian et al. | |
| 2006/0095058 A1 | 5/2006 | Sivan et al. | |
| 2006/0106109 A1 | 5/2006 | Burbank et al. | |
| 2006/0173517 A1 | 8/2006 | Gross | |
| 2006/0276871 A1 | 12/2006 | Lamson et al. | |
| 2007/0106233 A1 | 5/2007 | Huang et al. | |
| 2007/0185372 A1 | 8/2007 | Anderson et al. | |
| 2008/0039889 A1 | 2/2008 | Lamson et al. | |

FOREIGN PATENT DOCUMENTS

WO    WO 02/058577    8/2002

* cited by examiner

*Primary Examiner* — Roy Gibson
(74) *Attorney, Agent, or Firm* — Stein McEwen, LLP

(57) ABSTRACT

An implant system including a transurethral prostatic implant positioned in a prostate and including a lumen with an inner perimeter that surrounds an outer perimeter of a urethra at the prostate. The implant system may include a delivery tool including a shaft having a distal portion and an implant-holding portion proximal to the distal portion, the distal portion being sized for entry into a urethra, and the implant-holding portion being thicker than the distal portion, and an implant positioned on the implant-holding portion.

12 Claims, 4 Drawing Sheets

IMPLANT AND DELIVERY TOOL THEREFOR

CROSS-REFERENCE TO RELATED APPLICATIONS

The present application is a continuation of U.S. patent application Ser. No. 11/325,731, filed Jan. 5, 2006 now U.S. Pat. No. 7,632,297, which is a continuation of Ser. No. 10/736,740, filed Dec. 17, 2003, now U.S. Pat. No. 7,004,965.

FIELD OF THE INVENTION

The present invention relates generally to implants and delivery tools therefor, and particularly to an implant that is placed around a body lumen, such as but not limited to, a transurethral prostatic implant for treatment of benign prostatic hyperplasia (BPH).

BACKGROUND OF THE INVENTION

Benign prostatic hyperplasia (BPH) is a condition wherein a benign (non-cancerous) tumor with nodules enlarges the prostate gland. Although the growth is non-cancerous, as the tumor grows larger it can obstruct the urethra and interfere with the normal flow of urine.

Medications to treat BPH include alpha-1 blockers (doxazosin, prazosin, tamsulosin, and terazosin), which relax the muscles of the bladder neck, allowing easier urination. Finasteride is a drug that lowers prostate hormone levels, thus reducing the size of the prostate. Finasteride has been shown to increase urine flow rate and decrease the symptoms of BPH.

Surgery may be recommended for men with symptoms of incontinence, recurrent blood in the urine, urinary retention, and recurrent urinary tract infections. The choice of a specific surgical procedure is usually based on the severity of symptoms and the size and shape of the prostate gland.

Surgical treatment options include transurethral resection of the prostate (TURP), transurethral incision of the prostate (TUIP), and open prostatectomy. Other treatments include hyperthemia, laser therapy, and prostatic stents. Problems with stents are possible crustation, infection and epithelial irritation and inner growth.

Transurethral resection of the prostate (TURP) is the most common surgical treatment for BPH. TURP is performed by inserting a scope through the penis. The primary advantage of this procedure is that it does not involve an incision, thus reducing the risk of infection.

Other surgical approaches include the retropubic (behind the pubic structures) and suprapubic (above the pubic structures) open prostatectomies, which are done through an abdominal incision. The perineal surgical approach (through the region from the scrotum to the anus) is rarely used because the impotence rate after surgery may be as high as 50%.

Transureihral incision of the prostate (TUIP) is similar to TURP, but is usually performed in men who have a relatively small prostate. This procedure is usually performed on an outpatient basis and does not require a hospital stay.

The procedure is done through the penis without an incision. A small incision is made in the prostatic tissue to enlarge the lumen (opening) of the urethra and bladder outlet, thus improving the urine flow rate and reducing the symptoms of BPH. Eighty percent of the men who had this procedure reported some improvement in their symptoms. Possible complications include bleeding, infection, urethral stricture, and impotence.

An open prostatectomy is usually performed using general or spinal anesthesia. An incision is made through the abdomen or perineal area (i.e., through the pelvic floor, including the region from the scrotum to the anus). This is a lengthy procedure, and it usually requires a hospital stay of 5 to 10 days.

SUMMARY OF THE INVENTION

The present invention seeks to provide an innovative implant that is placed around a body lumen, as described more in detail hereinbelow. The implant of the invention is particularly useful in the treatment of BPH, and as such, a preferred embodiment is described hereinbelow that comprises a transurethral prostatic implant and delivery tool therefor. However, it is emphasized that the invention is not limited to a transurethral prostatic implant, and the invention may be used as an implant in other body lumens, such as but not limited to, blood vessels and lymph vessels.

There is thus provided in accordance with an embodiment of the present invention an implant system including a transurethral prostatic implant positioned in a prostate and including a lumen with an inner perimeter that surrounds an outer perimeter of a urethra at the prostate.

In accordance with an embodiment of the present invention the implant system includes a delivery tool including a shaft having a distal portion and an implant-holding portion proximal to the distal portion, the distal portion being sized for entry into a urethra, and the implant-holding portion being thicker than the distal portion, and an implant positioned on the implant-holding portion. (Again, the implant has a lumen with an inner perimeter greater in size than an outer perimeter of the urethra.)

Further in accordance with embodiments of the present invention, the implant may include a plurality of coils configured to corkscrew into tissue. The coils may or may not be continuous to one another. The coils may be coated with a substance. One or more of the coils may be energized to deliver RF energy or provide thermal energy. The implant-holding portion may be formed with screw threads corresponding to the pitch between the coils, and the implant may be initially positioned on the screw threads. A shoulder may be formed at a junction of the distal portion and the implant-holding portion. An implanting tool may be provided that includes a spiral pusher adapted for screwing onto the implant-holding portion of the shaft by rotation about a longitudinal axis of the shaft. Rotation of the implanting tool may cause the implant to unscrew off the implant-holding portion, advance distally off the shaft and corkscrew into tissue. The delivery tool may include a hollow lumen for passing therethrough at least one of a substance and a tool. The shaft may include a hollow lumen in fluid communication with a plurality of holes formed on a side wall of the shaft. A suction device may be in fluid communication with the holes that are on the side wall of the shaft.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENT

Figure 1:
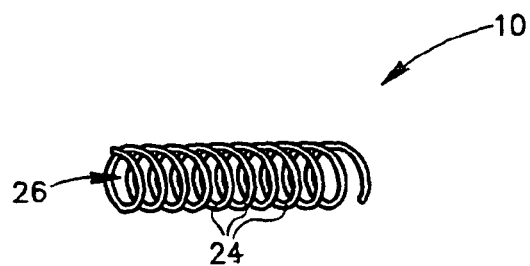
FIG. 1 is a simplified pictorial illustration of a transurethral prostatic implant, constructed and operative in accordance with an embodiment of the present invention.
Figure 2:
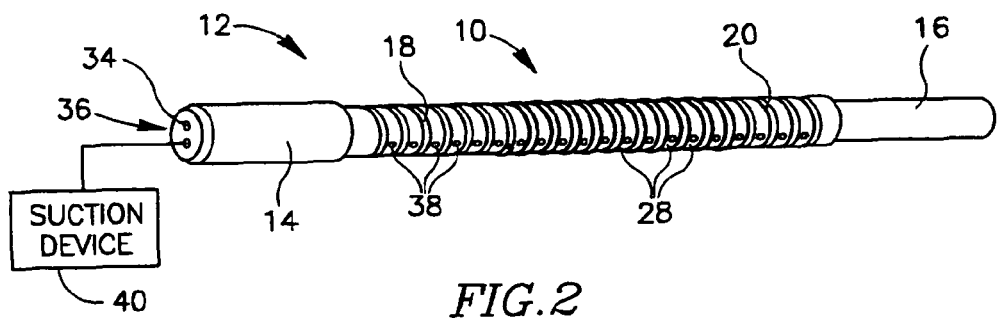
FIG. 2 is a simplified pictorial illustration of the transurethral prostatic implant of FIG. 1 mounted on a delivery tool, constructed and operative in accordance with an embodiment of the present invention.
Figure 3:
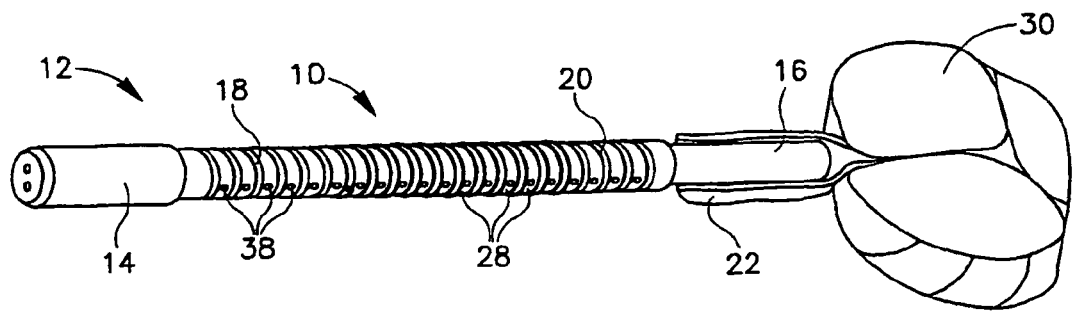
FIG. 3 is a simplified, partially cutaway illustration of the delivery tool of FIG. 2 being introduced into a urethra.

Reference is now made to FIGS. 1-3, which illustrate a transurethral prostatic implant 10 and delivery tool 12 therefor, constructed and operative in accordance with an embodiment of the present invention.

The delivery tool 12 may comprise a shaft 14 having a distal portion 16 and an implant-holding portion 18 proximal to the distal portion 16. A shoulder 20 may be formed at a junction of distal portion 16 and implant-holding portion 18. The distal portion 16 is sized for entry into a urethra 22 (FIG. 3). The implant-holding portion 18 is preferably thicker (e.g., larger in diameter) than the distal portion 16. The delivery tool 12 may be constructed of any suitable material, e.g., metal or plastic.

Transurethral prostatic implant 10 may be positioned on implant-holding portion 18. Implant 10 may be constructed of any suitable, medically-safe material, such as but not limited to, stainless steel, titanium, NITINOL and others. Implant 10 may comprise a plurality of coils 24 configured to corkscrew into tissue, as is described hereinbelow. For example, a distal, leading edge of the coils 24 may be sufficiently sharp to pierce tissue and corkscrew therein. The coils 24 may be continuous to one another, or alternatively, may be discrete coils. The coils 24 may be coated with a substance, such as but not limited to, a medication (e.g., beta blockers, antibiotics, etc.) or with an electrical insulator (e.g., TEFLON). One or more of the coils 24 (e.g., at the distal tip) may be energized to deliver RF energy, for example, to ablate tissue. Additionally or alternatively, one or more of the coils 24 (e.g., at the distal tip) may be energized to provide thermal energy (e.g., heating or cooling). The coils 24 may be of any shape or size, such as but not limited to, round, square, rectangular, etc.

Implant 10 has a lumen 26 with an inner perimeter greater in size than an outer perimeter of the urethra 22. The importance of this feature will become apparent hereinbelow.

The implant-holding portion 18 may be formed with screw threads 28 corresponding to the pitch (spacing) between coils 24. Accordingly, implant 10 may be initially positioned on screw threads 28.

Figure 7:
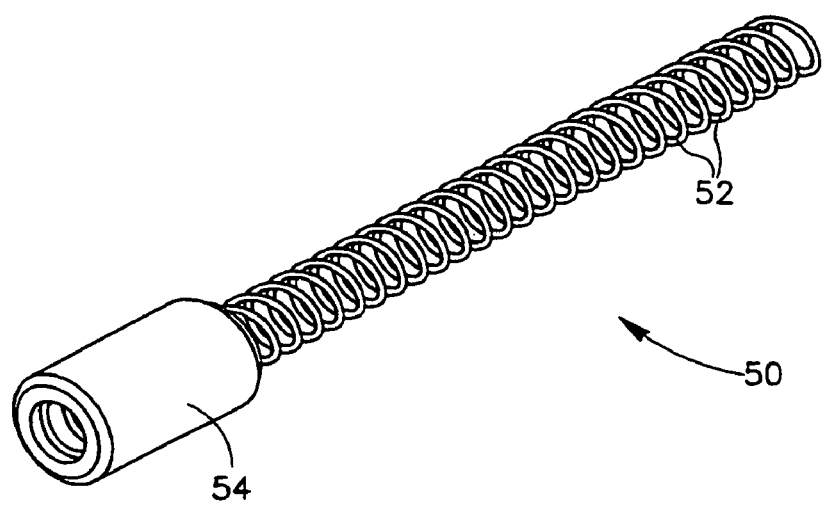
FIG. 7 is a simplified pictorial illustration of an implanting tool used to corkscrew the transurethral prostatic implant into tissue, constructed and operative in accordance with an embodiment of the present invention.
Figure 8:
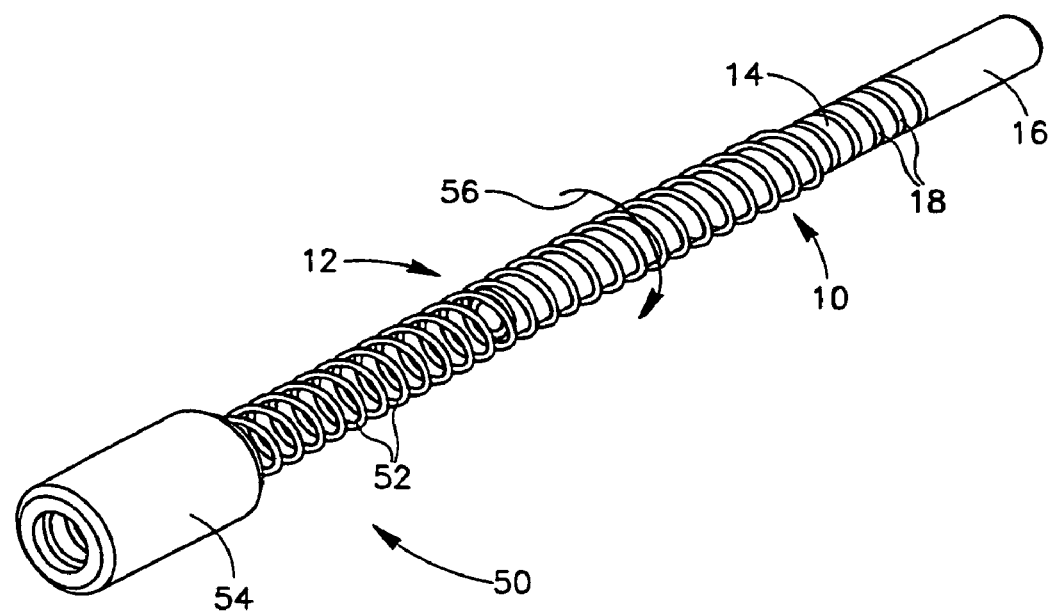
FIG. 8 is a simplified pictorial illustration of the implanting tool of FIG. 7 advancing the transurethral prostatic implant distally off the shaft of the delivery tool, in accordance with an embodiment of the present invention.

Reference is now made to FIGS. 7 and 8, which illustrate an implanting tool 50 used to advance transurethral prostatic implant 10 distally off the shaft 14 of the delivery tool 12, in accordance with an embodiment of the present invention. Implanting tool 50 may include a spiral pusher 52, constructed of a wire coil (e.g., stainless steel) with a pitch between coils corresponding to the pitch between coils 24. A proximal end of spiral pusher 52 may be mounted in a handle 54. As seen in FIG. 8, implanting tool 50 may be screwed onto the implant-holding portion 18 of shaft 14 by rotation about the longitudinal axis of shaft 14 in the direction of an arrow 56. As implanting tool 50 is rotated in the direction of arrow 56, it advances distally on shaft 14 and abuts against implant 10. Further rotation and distal advance of implanting tool 50 causes implant 10 to unscrew off implant-holding portion 18 and advance distally off shaft 14.

Reference is now made to FIGS. 3-6, which illustrate usage of the delivery tool 12. FIG. 3 illustrates the delivery tool 12 being introduced into the urethra 22.

Figure 4:
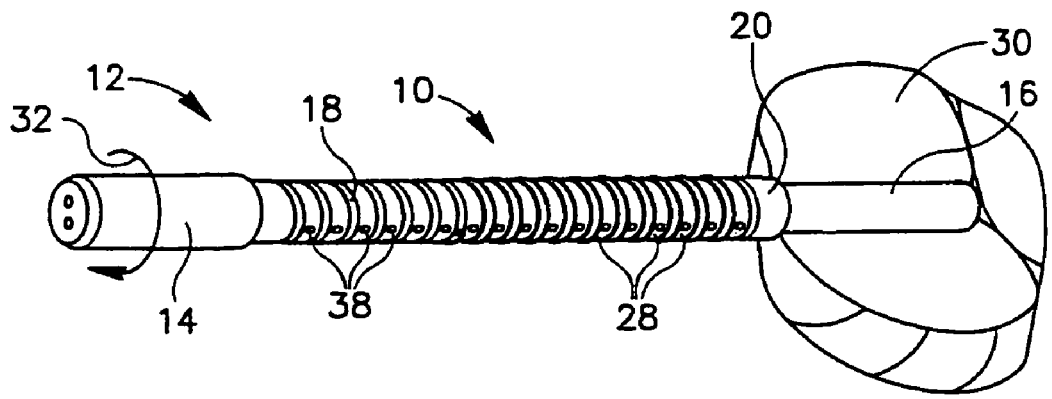
FIG. 4 is a simplified, partially cutaway illustration of the delivery tool of FIG. 2 after being introduced though the urethra up to a prostate.
Figure 5:
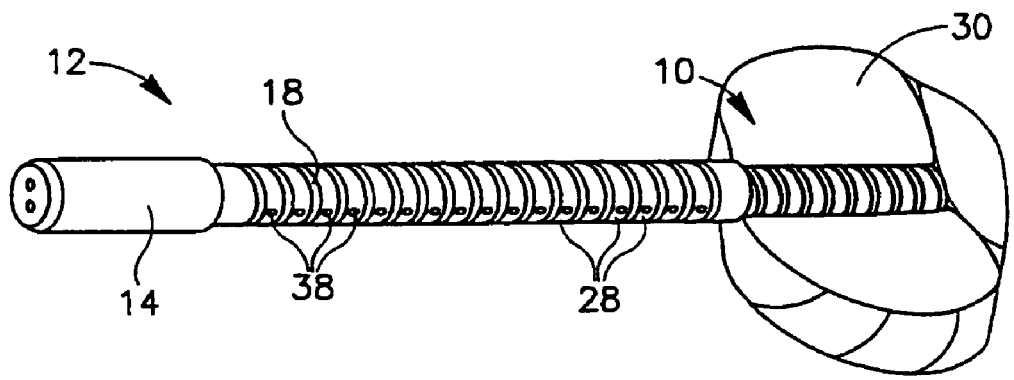
FIG. 5 is a simplified, partially cutaway illustration of the delivery tool of FIG. 2 introducing the transurethral prostatic implant into the urethra.
Figure 6:
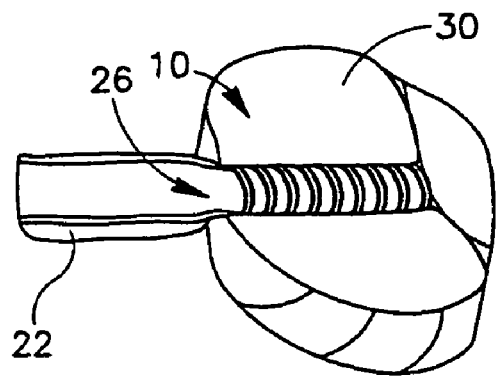
FIG. 6 is a simplified, partially cutaway illustration of the transurethral prostatic implant in place in the prostate and around the urethra, in accordance with an embodiment of the present invention.

FIG. 4 illustrates the delivery tool 12 having been introduced though the urethra 22 up to a prostate 30. At this point, shoulder 20 abuts against a surface of the prostate 30. Distal portion 16 opens the constricted urethra 22 to the desired diameter. As mentioned just before, suitable rotation and distal advance of implanting tool 50 (not shown in FIG. 4 for the sake of clarity) causes implant 10 to unscrew off implant-holding portion 18 and advance distally off shaft 14. As seen in FIG. 5, the implant 10 corkscrews into the prostate 30. Implant 10 is now positioned in the prostate 30 and the inner perimeter of lumen 26 surrounds the outer perimeter of the urethra 22 at the prostate 30. Thus, implant 10 supports the prostatic tissue surrounding the urethra 22 without touching the epithelium or other delicate tissue, and enlargens the area in the urethra 22 for urine to pass therethrough. Because the implant 10 does not contact the urethra 22, inflammation, crustation and disease may be reduced or prevented.

The delivery tool 12 may comprise a hollow lumen 34 for passing substances and/or tools therethrough, such as but not limited to, cooling fluid, medications, fiber optics, biopsy tools, optical devices (e.g., CCD) and/or imaging devices.

The shaft 14 may include a hollow lumen 36 in fluid communication with a plurality of holes 38 formed on a side wall of shaft 14 (such as but not limited to, distal portion 16). A suction device 40 may be in fluid communication with holes 38. By applying a vacuum (suction force) with suction device 40, the outer wall of the urethra 22 may be sucked into the hollow lumen 36 and help ensure that implant 10 surrounds and does not touch the outer wall of the urethra 22 when corkscrewing into the prostate 30.

Figure 9:
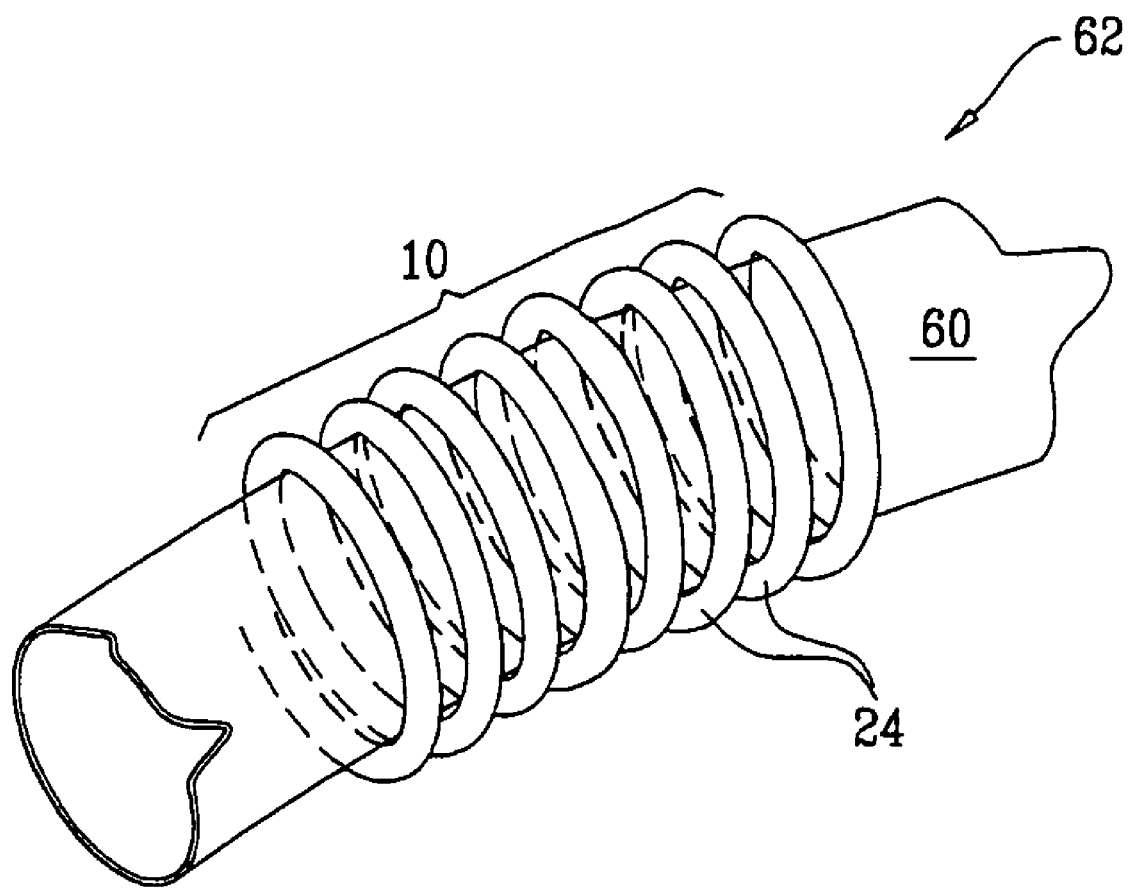
FIG. 9 is a simplified pictorial illustration of an implant, constructed and operative in accordance with an embodiment of the present invention, used to bolster a weakened blood vessel.

As mentioned above, the invention is not limited to the transurethral prostatic implant 10 described previously. Rather the invention may be used as an implant in other body lumens, such as but not limited to, blood vessels and lymph vessels. For example, as seen in FIG. 9, the implant 10 may be introduced to the site of an aneurysm (where there is a weakened wall 60 of a blood vessel 62), such as by means of a catheter or by as suitable surgical technique, wherein the coils 24 of implant 10 surround the wall 60 of the blood vessel 62. Implant 10 thus strengthens the weakened wall 60 and prevents further bulging outwards of the aneurysm. In such a case, the coils 24 may not necessarily corkscrew into some tissue, rather they envelope the aneurysm and bolster the blood vessel wall 60.

It will be appreciated by persons skilled in the art that the present invention is not limited by what has been particularly shown and described hereinabove. Rather the scope of the present invention includes both combinations and sub-combinations of the various features described hereinabove as well as variations and modifications which would occur to persons skilled in the art upon reading the specifications and which are not in the prior art.

What is claimed is:

1. A method, comprising:
advancing a delivery tool through a urethra of a patient;
from within the urethra, with the delivery tool, opening a portion of the urethra from a constricted diameter thereof to an opened diameter thereof; and
while the portion of the urethra is at the opened diameter, maintaining an area for urine to pass through the urethra, by implanting in tissue of a prostate, outside of the portion of the urethra, at least one implant advanced thereto by the delivery tool.

2. The method according to claim 1, further comprising enlarging the area for urine to pass through the urethra in conjunction with implanting the implant in the tissue of the prostate outside of the portion of the urethra.

3. The method according to claim 1, wherein implanting the implant in the tissue of the prostate outside of the portion of the urethra comprises supporting the tissue of the prostate outside of the portion of the urethra.

4. The method according to claim 1, wherein maintaining the area for urine to pass through the urethra comprises supporting the tissue of the prostate outside of the portion of the urethra.

5. The method according to claim 1, wherein opening the portion of the urethra comprises pushing radially against the portion of the urethra, and wherein maintaining the area for urine to pass through comprises supporting the tissue of the prostate outside of the portion of the urethra.

6. The method according to claim 5, wherein supporting the tissue of the prostate outside of the portion of the urethra comprises maintaining the opened diameter of the portion of the urethra.

7. Apparatus, comprising:
at least one transurethrally-deliverable prostatic implant;
a delivery tool advanceable through a urethra of a patient, the tool comprising:
an implant-holding portion configured to hold the implant during advancement of the delivery tool through the urethra; and
a urethra-opening portion thereof configured to open a portion of the urethra from a constricted diameter thereof to an opened diameter thereof,
the delivery tool being configured to implant the at least one implant in tissue of a prostate, outside of the portion of the urethra while the portion of the urethra is at the opened diameter, and
the implant being configured to maintain an area for urine to pass through the urethra.

8. The apparatus according to claim 7, wherein the implant-holding portion has a longest dimension measured at its cross-section that is different from a longest dimension measured at a cross-section of the urethra-opening portion.

9. The apparatus according to claim 7, wherein the implant comprises a plurality of coils configured to corkscrew into the tissue of the prostate.

10. The apparatus according to claim 9, wherein the plurality of coils define a lumen with an inner perimeter sized to surround an outer perimeter of the portion of the urethra.

11. The apparatus according to claim 7, wherein the urethra-opening portion is configured to push radially against at least the portion of the urethra, and wherein the implant is configured to maintain the area for urine to pass through by supporting the tissue of the prostate outside of the portion of the urethra.

12. The method according to claim 11, wherein the implant is configured to maintain the opened diameter of the portion of the urethra.

* * * * *